US005789681A

United States Patent [19]
Angley et al.

[11] Patent Number: 5,789,681
[45] Date of Patent: Aug. 4, 1998

[54] ARRESTING MATERIAL TEST APPARATUS AND METHODS

[75] Inventors: Richard D. Angley, Aston; Michael S. Ciesielski, Broomall; Christopher T. Dial, Lansdowne; Peter T. Mahal, Ardmore, all of Pa.; Robert F. Cook, Chipley, Fla.

[73] Assignee: Datron Inc., Garland, Tex.

[21] Appl. No.: 796,968

[22] Filed: Feb. 7, 1997

[51] Int. Cl.$^6$ ................................................ G01N 3/00
[52] U.S. Cl. ................................... 73/803; 73/82
[58] Field of Search .................. 73/12.13, 12.01, 73/12.08, 786, 803, 844, 862.541, 866, 81, 82, 85

[56] References Cited

U.S. PATENT DOCUMENTS

| | | | |
|---|---|---|---|
| 3,498,114 | 3/1970 | Garber et al. | 73/82 |
| 3,566,668 | 3/1971 | Browning et al. | 73/12.13 |
| 3,732,725 | 5/1973 | Allen, Jr. et al. | 73/803 X |
| 3,867,159 | 2/1975 | Ergene . | |
| 3,894,426 | 7/1975 | Kpof | 73/82 |
| 4,182,191 | 1/1980 | Ikdea | 73/803 |
| 4,640,120 | 2/1987 | Garritano et al. | 73/12.13 |
| 4,649,735 | 3/1987 | Pihlaja | 73/82 X |
| 5,048,320 | 9/1991 | Mitsuhashi et al. | 73/82 X |
| 5,193,764 | 3/1993 | Larratt . | |
| 5,241,993 | 9/1993 | Stevens . | |
| 5,419,632 | 5/1995 | Stevens . | |
| 5,616,857 | 4/1997 | Merck, Jr. et al. | 73/82 |

OTHER PUBLICATIONS

ACI Committee 523, "Guide for Cast-in-Place Low Density Concrete", *ACI Journal*, Sep. 1967.
*Standard Test Method for Compressive Strength of Lightweight Insulating Concrete*, (C495-86), American Society for Testing and Materials, Dec. 1986.
Cook, Robert F., *Evaluation of a Foam Arrestor Bed for Aircraft Safety Overrun Areas*,(UDR-TR-88-07), University of Dayton Research Institute, Jan. 1988.

McMichael, Steve and Fisher, Steve, "Understanding Materials with Instrumented Impact", *Mechanical Engineering*, Apr. 1989.
Balaguru, P. and Ramakrishnan, Seetharamen, *Properties of Lightweight Cement Composite Containing Ceramic Spheres*, (Civil Engineering Report No. 92–11), The State University of New Jersey, Rutgers, Nov. 1992.
"Quality Assurance of Batch Mixed Cellular Concrete", Cellufoam Concrete Systems, Dec. 1994.
*Preliminary Soft Ground Arrestor Design for JFK International Airport*, (Draft of Final Report DOT/FAA/CT-95), Mar. 1995.

(List continued on next page.)

*Primary Examiner*—Elizabeth L. Dougherty
*Attorney, Agent, or Firm*—Kenneth P. Robinson

[57] ABSTRACT

Arresting material test apparatus, test probes and test methods enable testing of compressive gradient strength of cellular concrete, and materials having similar characteristics, on a continuous basis from the surface of a section to a typical internal penetration depth of at least 60 percent of thickness. Previous testing of cellular concrete typically focused on testing to confirm a minimum structural strength prior to structural failure or shattering of a test sample. For an aircraft arresting bed, for example, cellular concrete must exhibit a compressive gradient strength in a relatively narrow precalculated range continuously from the surface to penetration depth equal to 60 to 80 percent of sample thickness. Precalculated and controlled compressive gradient strength is critical to enabling an aircraft to be safely stopped within a set distance, without giving rise to drag forces exceeding main landing gear structural limits. New test apparatus, test probes with post-compression build-up relief and test methods are described to enable such testing and recordation of data showing the gradient of compressive strength as it increases from the surface of a test sample to a predetermined depth of penetration. Resulting compressive gradient strength data is representative of performance of cellular concrete sections in decelerating an aircraft.

34 Claims, 5 Drawing Sheets

OTHER PUBLICATIONS

Brochure: "Structural and Nonstructural Mearlcrete Cellular Concrete Applications and Properties", The Mearl Corporation, Dec. 1987.

Brochure: "E-SORB Hollow Sphere Composites for Energy Absorption", Microcel Technology, Inc., date unknown.

Brochure: "Geotechnical Grouting Applications Using Low Density Cellular Concrete", Pacific International Grout Co., date unknown.

Brochure: "Light-Weight Foam Technology", Zementschaum-Technik International GmbH, date unknown.

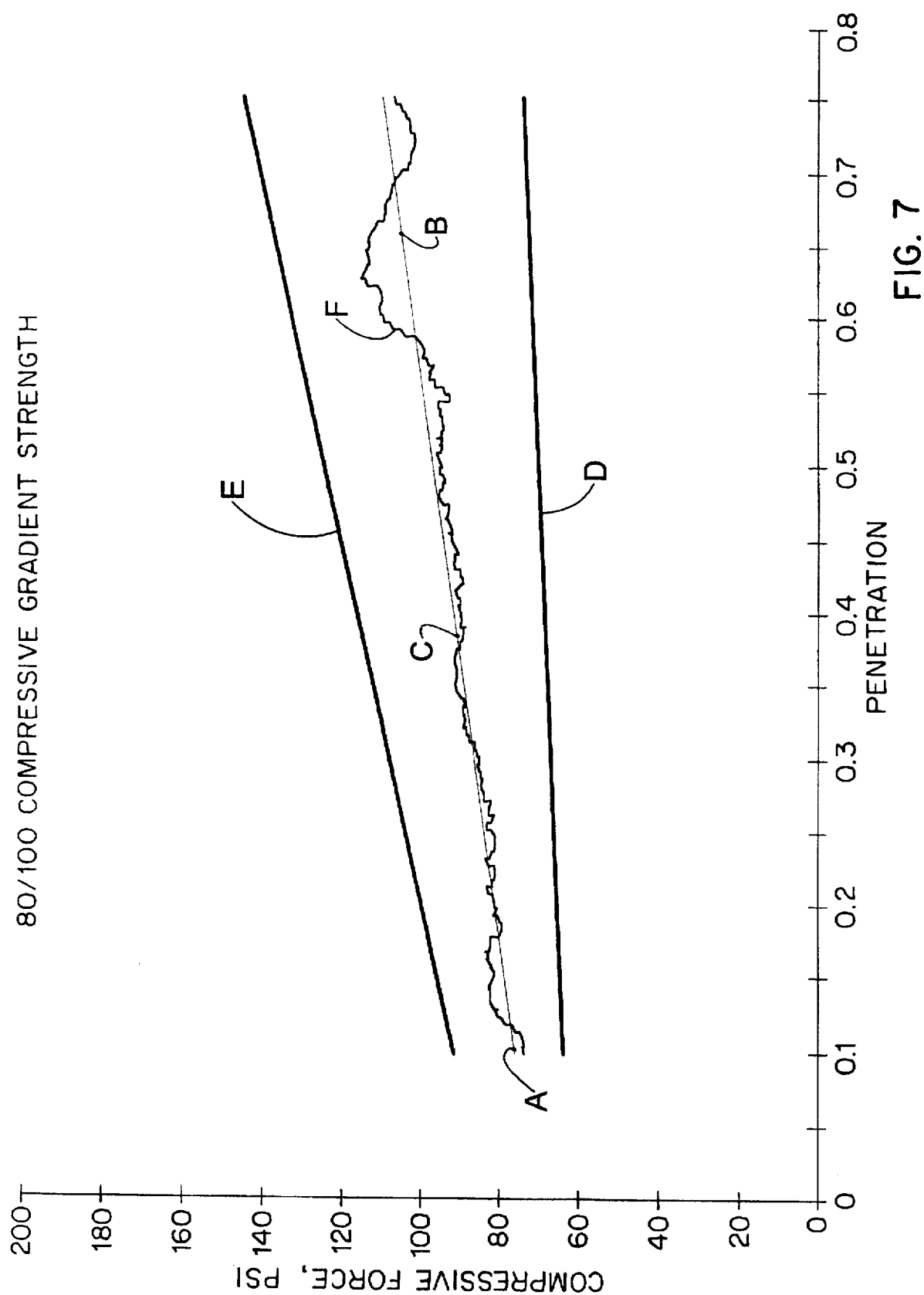

ARRESTING MATERIAL TEST APPARATUS AND METHODS

BACKGROUND OF THE INVENTION

This invention relates to systems for slowing travel of vehicles and, more particularly, to test apparatus and methods to test cellular concrete intended for use in arresting bed systems to safely decelerate an aircraft which runs off the end of a runway.

Aircraft can and do overrun the ends of runways raising the possibility of injury to passengers and destruction of or severe damage to the aircraft. Such overruns have occurred during aborted take-offs or while landing, with the aircraft traveling at speeds to 80 knots. In order to minimize the hazards of overruns, the Federal Aviation Administration (FAA) generally requires a safety area of 1,000 feet in length beyond the end of the runway. Although this safety area is now an FAA standard, many runways across the country were constructed prior to its adoption and are situated such that water, roadways or other obstacles prevent economical compliance with the one thousand foot overrun requirement.

Several materials, including existing soil surfaces beyond the runway have been assessed for their ability to decelerate aircraft. Soil surfaces are very unpredictable in their arresting capability because their properties are unpredictable. For example, very dry clay can be hard and nearly impenetrable, but wet clay can cause aircraft to mire down quickly, cause the landing gear to collapse, and provide a potential for passenger and crew injury as well as greater aircraft damage.

A 1988 report addresses an investigation by the Port Authority of New York and New Jersey on the feasibility of developing a plastic foam arrestor for a runway at JFK International Airport. In the report, it is stated that analyses indicated that such an arrestor design is feasible and could safely stop a 100,000 pound aircraft overrunning the runway at an exit velocity up to 80 knots and a 820,000 pound aircraft overrunning at an exit velocity up to 60 knots. The report states that performance of an appropriate plastic foam arrestor configuration was shown to be potentially "superior to a paved 1,000 foot overrun area, particularly when braking is not effective and reverse thrust is not available." As is well known, effectiveness of braking may be limited under wet or icy surface conditions. (University of Dayton report UDR-TR-88-07, January 1988.)

More recently, an aircraft arresting system has been described in U.S. Pat. No. 5,193,764 to Larrett et al. In accordance with the disclosure of that patent, an aircraft arresting area is formed by adhering a plurality of stacked thin layers of rigid, friable, fire resistant phenolic foam to each other, with the lower-most layer of foam being adhered to a support surface. The stacked layers are designed so that the compressive resistance of the combined layers of rigid plastic foam is less than the force exerted by the landing gear of any aircraft of the type intended to be arrested when moving into the arresting area from a runway so that the foam is crushed when contacted by the aircraft. The preferred material is phenolic foam used with a compatible adhesive, such as a latex adhesive.

Tests of phenolic foam based arrestor systems indicate that while such systems can function to bring aircraft to a stop, the use of the foam material has disadvantages. Major among the disadvantages is the fact that foam, depending upon its properties, can typically exhibit a rebound property. Thus, it was noted in phenolic foam arresting bed testing that some forward thrust was delivered to the wheels of the aircraft as it moved through the foamed material as a result of the rebound of the foam material itself.

Foamed or cellular concrete as a material for use in arresting bed systems has been suggested and undergone limited field testing in the prior art. Such testing has indicated that cellular concrete has good potential for use in arresting bed systems, based on providing many of the same advantages as phenolic foam while avoiding some of phenolic foam's disadvantages. However, the requirements for an accurately controlled crushing strength and material uniformity throughout the arresting bed are critical and, so far as is known, the production of cellular concrete of appropriate characteristics and uniformity has not previously been achieved or described. Production of structural concrete for building purposes is an old art involving relatively simple process steps. Production of cellular concrete, while generally involving simple ingredients, is complicated by the nature and effect of aeration, mixing and hydration aspects, which must be closely specified and accurately controlled if a uniform end product, which is neither too weak nor too strong, is to be provided for present purposes. Discontinuities, including areas of weaker and stronger cellular concrete, may actually cause damage to the vehicle that is being decelerated if, for example, deceleration forces exceed wheel support structure strength. Such non-uniformity also results in an inability to accurately predict deceleration performance and total stopping distance. In one recent feasibility test utilizing commercial grade cellular concrete, an aircraft instrumented for recording of test data taxied through a bed section and load data was acquired. Even though steps had been taken to try to provide production uniformity, samples taken and aircraft load data from the test arresting bed showed significant variations between areas where the crush strength was excessively high and areas where it was excessively low obviously, the potential benefit of an arresting system is compromised, if the aircraft is exposed to forces that could damage or collapse the main landing gear.

Thus, while arresting bed systems have been considered and some actual testing of various materials therefor has been explored, practical production and implementation of either an arresting bed system which within specified distances will safely stop aircraft of known size and weight moving at a projected rate of speed off of a runway, or of materials suitable for use therein, have not been achieved. The amount of material, and the geometry in which it is formed to provide an effective arresting bed for vehicles of a predetermined size, weight, and speed, is directly dependent upon the physical properties of the material and, in particular, the amount of drag which will be applied to the vehicle as it moves through the bed crushing or otherwise deforming the material. Computer programming models or other techniques may be employed to develop drag or deceleration objectives for arresting beds, based upon the calculated forces and energy absorption for aircraft of particular size and weight, in view of corresponding landing gear strength specifications for such aircraft. However, the models must assume that the arresting bed is constructed of a material having a section to section and batch to batch uniformity of characteristics, such as strength, durability, etc., to produce uniform results with a predictable amount of energy absorption (drag) when contacted by the portions of the aircraft (or other vehicle) which are bearing the load of the vehicle through the bed (e.g., the wheels of an aircraft as it moves through the bed after having overrun the runway).

One of the potential benefits of the use of foamed or cellular concrete in arresting bed systems is that the material itself is capable of being produced in a variety of different ways using numerous different starting materials. For prior types of applications not relating to vehicle deceleration the concrete has been produced by using a particular type of cement (usually Portland) which is combined with water, a foaming agent, and air to produce a cellular concrete. However, a significant distinguishing requirement separates such prior applications of cellular concrete from production of a product suitable for use in an arresting bed. In prior applications, the objectives are typically reduced weight or cost, or both, while providing a predetermined minimum strength with the more strength the better. Prior applications have typically not required that cellular concrete be produced to strict standards of both maximum strength and minimum strength. Also, prior applications have not required a high degree of uniformity of material, provided basic strength objectives are met. Even for prior applications of cellular concrete, it is known that the amount and type of cement, the water/cement ratio, the amount and type of foaming agent, the manner in which the materials are combined, processing conditions and curing conditions can all have critical effects on the resulting properties of the cellular concrete. No necessity to refine production to the levels required to produce cellular concrete suitable for vehicle arresting beds has been presented by prior applications.

Thus, it is one thing to specify objectives as to mechanical properties of materials appropriate to obtain the desired deceleration on entry of an airplane or other vehicle into the arresting bed. However, the capability of consistently producing cellular concrete material which will actually have the required properties of predetermined strength and uniformity is not known to have been previously achieved.

One substantial problem in the art is the lack of established techniques for production of cellular concrete in the low strength range, in a uniform fashion to very tight tolerances, to enable construction of an entire arresting bed consistently having the desired mechanical properties throughout its geometry. While poured in place cellular concrete has been suggested, no practical design for successfully implementing a cellular concrete arresting bed has previously been provided.

Another problem is determining in advance what mechanical forces the vehicle will actually experience as it moves through foamed concrete of a particular grade of manufacture. The mechanical properties of interest are not the strength, per se, of the material, but rather the decelerating force experienced by an object moving through the material as the material is deformed. Most conventional testing of concrete samples measures the fracture strength of the material, in order to establish that at least a specified load will be supported. By contrast, in arresting bed technology it is the energy absorbed on a continuing basis during compressive failure of the material which is the important characteristic (i.e., actual strength during continuing compressive failure). Without an appropriate test methodology which can be used to determine on a continuing basis the compressive strength that will be supplied by foamed concrete of a particular formula, production technique, curing, and design, the art would be left with the requirement of building very costly arresting bed structures with a variety of different cellular concrete samples in an effort to determine which of these, when used as an actual arresting bed, functions in a manner that could be predicted. More particularly, since, in the past, applications for structural cellular concrete could be supported by minimum strength testing, neither suitable test methods nor apparatus have been provided to enable reliable testing of compressive strength continuously over a depth of penetration from the surface of a section of cellular concrete and continuing to an internal penetration depth up to eighty percent of section thickness.

Objects of the invention are to provide new and improved test apparatus and methods for testing cellular concrete arresting material, and such test apparatus and methods which provide one or more of the following advantages and capabilities:

reliable determination of compressive gradient strength which will be experienced when decelerating a moving object;

compressive strength testing without structural collapse of a test sample;

determination of compressive gradient strength from the surface of a sample continuously to an internal depth of penetration of the order of 70 percent of sample thickness;

recording of compressive failure test pressure and penetration depth on a continuous basis;

use of an improved test probe head continuously driven by a penetration shaft; and use of a penetration shaft having a shaft portion of restricted cross section to reduce post-compression material build-up effects which can distort accuracy of data obtained.

SUMMARY OF THE INVENTION

In accordance with the invention, arresting material test apparatus, to test compressive gradient strength continuously from the surface to an internal depth of penetration within compressible arresting material, includes a penetration shaft having a length not less than the internal depth of penetration and a cross-sectional size. A test probe head is connected to the penetration shaft and has a compressive contact surface. The penetration shaft includes a constricted shaft portion, beginning behind the test probe head and continuing for at least a part of the length of the penetration shaft. This constricted shaft portion typically has a cross-sectional area at least ten percent smaller than the area of the contact surface of the test probe, in order to reduce post-compression material build-up behind the test probe head and data distortion resulting from such build-up.

A drive mechanism is coupled to the penetration shaft to displace the shaft to drive the test probe head to the internal depth of penetration within arresting material. A displacement sensing device coupled to the penetration shaft is provided to sense displacement thereof. A load sensing device coupled to the penetration shaft senses the pressure exerted against the test probe contact surface as it compresses arresting material to the internal depth of penetration. The apparatus also includes a data acquisition device responsive to pressure sensed by the load sensing device and responsive to the depth of penetration of the test probe contact surface to provide data representative of continuous measurement of compressive gradient strength of compressible arresting material subject to test.

Also in accordance with the invention, an arresting material test probe, suitable to test compressive gradient strength continuously from the surface to an internal depth of penetration within compressible arresting material, includes a penetration shaft, test probe head and constricted shaft portion as described above. The cross-sectional area and length of the constricted shaft portion are selected as appropriate to reduce post-compression build-up effects behind the contact surface as it travels from the surface to an internal depth of penetration within arresting material under test. Such depth of penetration may typically be at least 60 percent of the thickness of a section of arresting material to be tested.

Further in accordance with the invention, a method for continuous compressive failure testing of a cellular concrete section suitable for vehicle arresting use, includes the steps of:

(a) providing a penetration shaft bearing a test probe head with a contact surface having a contact surface area;

(b) providing a test section of cellular concrete having a thickness and having a cross-sectional area at least twenty times larger than the contact surface area;

(c) supporting the test section longitudinally;

(d) driving the contact surface of the test probe head longitudinally into the test section from a surface to an internal depth of penetration within the test section;

(e) monitoring on a continuous basis the displacement of the test probe head; and (f) monitoring the compressive force on said contact surface at a plurality of intermediate depths of penetration within the test section.

For a better understanding of the invention, together with other and further objects, reference is made to the accompanying drawings and the scope of the invention will be pointed out in the accompanying claims.

BRIEF DESCRIPTION OF THE DRAWINGS

FIGS. 6 and 7 show test data obtained using the FIG. 1 apparatus and FIG. 5 method, in terms of compressive force indicated along the ordinate versus percentage of penetration indicated along the abscissa for samples of cellular concrete of two different strengths.

DETAILED DESCRIPTION OF THE INVENTION

Figure 1:
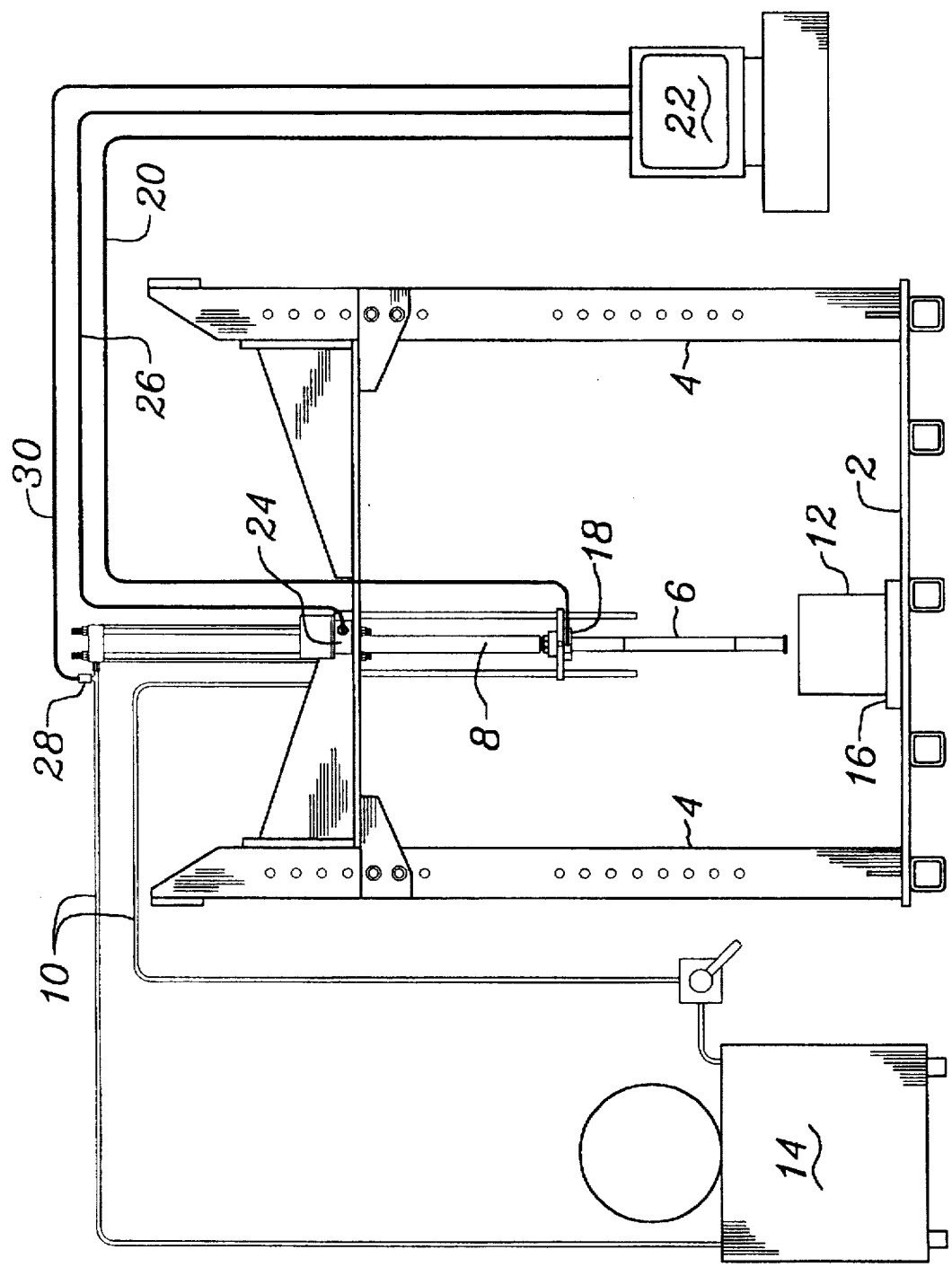
FIG. 1 illustrates an embodiment of arresting material test apparatus in accordance with the invention.

The use of cellular concrete in arresting bed applications requires the material to be generally uniform in its resistance to deformation since it is the predictability of forces acting on the surface of contacting members of the vehicle which is being decelerated that allows the bed to be designed, sized and constructed in a manner which will ensure acceptable performance. In order to obtain such uniformity, there must be careful selection and control of the ingredients used to prepare the cellular concrete, the conditions under which it is processed, and its curing regime.

The ingredients of cellular concrete are generally a cement, preferably Portland cement, a foaming agent, and water. Relatively fine sand or other materials can also find application in some circumstances, but are not used in presently preferred embodiments. For present purposes, the term "cellular concrete" is used as a generic term covering concrete with relatively small internal cells or bubbles of a fluid, such as air, and which may include sand or other material, as well as formulations not including such sand or other material.

There are many known methods for producing cellular concrete. In general the process includes the steps of mixing the foam concentrate with water, generating foam by inducing air, adding the resulting foam to the cement slurry or cement/aggregate slurry mix, and thoroughly blending the foam and cement slurry in a controlled manner that results in a homogeneous mixture with a significant amount of voids or "cells" which keep the density of the material relatively low as compared to other types of concrete. Because the application of cellular concrete to arresting bed applications requires a general uniformity of material properties, uniform foaming, mixing, and setting of the materials is of extreme importance.

Construction of the arresting bed system can be accomplished by producing the cellular concrete at a central production facility or at the site of the bed and pouring the concrete into forms of appropriate dimensions to achieve the desired geometry for the system. However, in the interests of uniformity of material characteristics and overall quality control, it has been found preferable to cast sections of the overall bed using forms of appropriate size and then transport the sections to the site and install them to form the overall configuration of the bed. In the latter case, such units or sections, in the form of blocks of predetermined sizes, can be produced and held until completion of quality control testing. The blocks can then be transported to the site, placed in position and adhered to the runway safety area using asphalt, cement grout, or other suitable adhesive material, depending on the construction materials of the safety area itself.

DEFINITION OF "COMPRESSIVE GRADIENT STRENGTH" OR "CGS"

The term "compressive strength" (not CGS) is normally understood to mean the amount of force (conventionally measured in pounds per square inch) which, when applied at a vector normal to the surface of a standardized sample, will cause the sample to fail. Most conventional test methods specify test apparatus, sampling procedures, test specimen requirements (including size, molding, and curing requirements) rates of loading and record keeping requirements. An example is ASTM C 495-86 "Standard Method for Compressive Strength of Lightweight Insulating Concrete." While such conventional test methods are useful when designing structures that are required to maintain structural integrity under predicted load conditions (i.e., have at least a minimum strength), the object of arresting bed systems is to fail in predictable specified manner, thereby providing controlled, predictable resistive force as the vehicle deforms the cellular concrete (i.e., a specific compressive gradient strength). Thus, such conventional testing focuses on determining strength up to a point of failure, not strength during compressive failure. Stated more simply, knowing what amount of force will shatter a specimen of cellular concrete material does not answer the critical question of what amount of drag or deceleration will be experienced by a vehicle moving through an arresting bed system. In contrast to a "one time" fracture strength as in the prior art, for present purposes testing must evaluate a continuous compressive failure mode as a portion of a specimen is continuously compressed to about twenty percent of its original thickness. Equipment and methods suitable for such continuous testing as appropriate for present purposes have generally not been previously available.

Because of the wide range of variables available in materials and processing of cellular concretes, and the size and cost of constructing arresting beds for testing, it is imperative that accurate test information be available to predict the amount of resistive force a particular variety of cellular concrete, processed and cured in a certain way, will provide when used in an arresting bed system. By developing new test methodology to focus the resulting data on measurement of the resistive force occurring during continuous compressive failure of a sample, instead of simple one-time "compressive strength", new test methods and apparatus have been developed to enable reliable testing and confirmation of appropriate cellular concrete materials and process variables. As a result, it has been determined that the compressive force needed to crush cellular concrete to 20 percent of its original thickness varies with the depth of penetration. This characteristic, which the present inventors term "compressive gradient strength" or "CGS" must be accurately specified in order to construct a cellular concrete vehicle arresting bed having known deceleration characteristics to safely slow an aircraft.

The test method and equipment of the present invention provide load and deformation data for test samples of cellular concrete, or materials with similar characteristics, that can be used to accurately predict how an arresting bed constructed from the same material will perform. Thus, a penetration type test method where the compressive strength of a sample of cellular concrete is gauged not by applying a force that will fracture a sample, but rather will continuously report information on resistive forces generated as a test probe head having a specified compressive contact surface is moved through a volume of cellular concrete, is key to obtaining the data necessary to formulate and use cellular concrete in arresting bed applications. As thus measured, CGS will vary over a range with penetration depth, resulting in a gradient value (such as 60/80 CGS) rather than a simple singular fracture value as in prior tests.

For present purposes, the term "compressive gradient strength" (or "CGS") is used to refer to the compressive strength of a section of cellular concrete from a surface and continuing to an internal depth of penetration which may typically be 66 percent of the thickness of the section. As thus defined, CGS does not correspond to compressive strength as determined by standard ASTM test methods.

FIG. 1 TEST APPARATUS

Referring now to FIG. 1, there is illustrated an embodiment of arresting material test apparatus in accordance with the invention. As will be described further, the FIG. 1 apparatus is arranged to test compressive gradient strength continuously from the surface to an internal depth of penetration within a sample section of compressible arresting material. As shown, there is included a structural platform base 2 suitable to support the bottom of a test section and form a test support structure in combination with side frame members 4.

A piston, in the form of penetration shaft 6 is slidably engaged in cylinder 8 and arranged for activation via fluid coupled through hydraulic lines 10. The configuration is such that a shaft 6 can be driven down toward a test section 12 of cellular concrete or other suitable material in reaction to activation of hydraulic pressure source 14. Test section 12 is supported during test by a bottom bearing block 16 resting on base 2. A test probe head mounted at the bottom of penetration shaft 6 will be described with reference to FIGS. 2–4. It will thus be appreciated that hydraulic cylinder 8, fed by lines 10 from hydraulic pressure source 14, comprise one form of drive mechanism coupled to penetration shaft 6 and provide the capability of continuously displacing shaft 6 to drive a test probe head to an internal depth of penetration within an arresting material test section 12.

As illustrated, the test apparatus further includes a load sensing device, shown as load cell 18. In known manner, load cell 18 is arranged to measure the force exerted upon penetration shaft 6 and the contact surface of the test probe head as it is displaced into, and causes compressive failure of, the cellular concrete of test section 12. Alternatively, the measured force may be considered to be a measure of the resistance provided by the cellular concrete against the contact surface of the test probe head during compressive failure of test section 12. Forces measured by the load cell comprising load sensing device 18 are continuously monitored and can be recorded in terms of force or pressure during test via data line 20 coupled to a data acquisition device 22. In FIG. 1, the test apparatus also includes a displacement sensing device, shown as a linear potentiometer 24, arranged so that its impedance varies with changes in the position of penetration shaft 6. Displacement sensing device 24 is coupled to data acquisition device 22 via data line 26 to enable displacement of shaft 6 to be continuously monitored and recorded during test. In the illustrated test apparatus, hydraulic pressure as sensed by a pressure sensing device, shown as pressure transducer 28, is also monitored and recorded via data line 30.

Figures 2, 3:
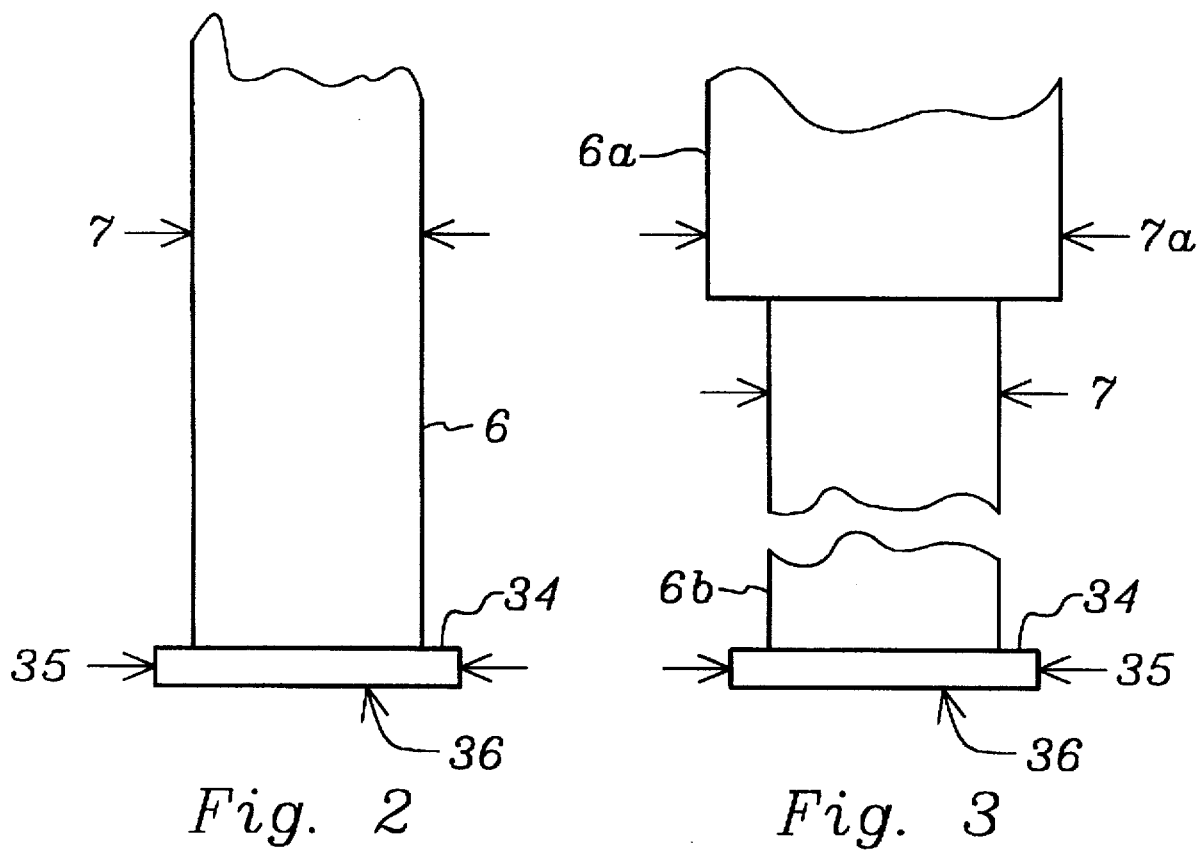
FIGS. 2 and 4 are respectively side and bottom views of a test probe head and portion of an associated penetration shaft utilizing the invention.
FIG. 3 is a side view showing a test probe head mounted to a penetration shaft of an alternative construction in accordance with the invention.
Figure 4:
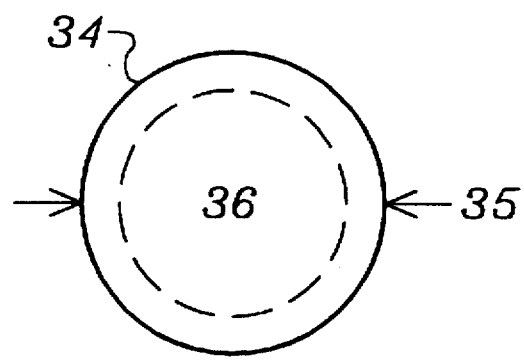

With reference now to FIGS. 2–4, there are shown in greater detail two exemplary configurations of an arresting material test probe in accordance with the invention, which is suitable to test compressive gradient strength continuously from the surface to an internal depth of penetration within arresting material. The test probe comprises a penetration shaft and a test probe head mounted at the lower end thereof. FIG. 2 shows the lower portion of a penetration shaft 6 having an overall length not less than the depth of internal penetration during testing, and a cross-sectional size represented by diameter 7. Penetration shaft 6 may typically be formed of steel and have a circular cylindrical form. Test probe head 34 is suitably connected to the lower end of shaft 6 (e.g., fixed thereto by welding, screwed into the end, etc.) so as to remain in position when exposed to longitudinal pressure. Test probe head 34 has a compressive contact surface 36, which may be hardened or otherwise suitable for compression of cellular concrete or other material without excessive deformation of surface 36. The size of contact surface 36, represented by diameter 35 indicated in the bottom view of FIG. 4, is larger than the cross-sectional size of a constricted shaft portion of penetration shaft 6. In FIG. 2 it will be seen that contact surface diameter 35 is larger than diameter 7 of shaft 6, which in this example is of a uniform diameter over its length. FIG. 3 shows an alternative configuration. In FIG. 3 penetration shaft 6a has a basic diameter 7a which mates with hydraulic cylinder 8 of FIG. 1. Penetration shaft 6a includes a restricted shaft portion 6b of smaller cross-sectional area, which begins behind test probe head 34 and continues for at least a portion of the length of the penetration shaft. Thus, with reference to FIG. 2, it will be seen that in the first configuration the restricted shaft portion having a reduced cross-sectional area, relative to contact surface 36, effectively extends for the full length of the penetration shaft, as also illustrated in FIG. 1. In FIG. 3, the restricted shaft portion represents only part of the length of shaft 6a. Pursuant to the invention it has been found that providing a restricted shaft portion extending behind the test probe head is effective to reduce potentially error-producing effects of post-compression build-up of particles of cellular concrete behind the contact surface as it travels into the arresting material under test. Preferably, the restricted shaft portion will have a length at least equal to the intended penetration depth. This feature has been found to enhance the accuracy and reliability of test results as an indication of actual compressive gradient strength to be experienced in use of arresting material.

A presently preferred configuration of test probe head 34 includes a flat circular contact surface 36 approximately 2 inches in diameter, with the restricted shaft portion (6 or 6b) behind head 34 having a cross-sectional area 10 to 50 percent smaller than the contact surface and continuing behind the test probe head 34 for a distance at least equal to the depth of penetration. The construction should have a basic structural integrity and contact surface hardness adequate to survive compressive pressures of at least 100 and preferably 500 pounds per square inch (psi) without failure or significant surface distortion. In other embodiments, the contact surface 36 may have a hexagonal or other suitable shape and be of any appropriate size. However, in this regard it is presently considered preferable that the size of contact surface 36, relative to the cross-sectional size of test portion 12, be such that testing may be completed without general structural failure or shattering of the test sample such as fall-away of side portions of test portion 12, prior to about 70 percent penetration. Pursuant to the invention, in order to obtain accurate results indicative of compressive gradient strength in arresting bed use, it is presently preferred that test portion 12 be supported only from the bottom, without lateral support, banding or enclosure, and should remain intact during testing except for internal compressive failure along the path of test probe head 34. General structural failure or shattering of the test sample after 70 or 80 percent penetration is typically not a matter of concern as to validity of test results. By using a test method where the sample is unconstrained as the piston penetrates and exerts resulting stresses, a closer approximation to arresting test bed performance is achieved since there will not be a constraint or reflection of stress forces caused by the cellular concrete or other material under test being forced up against an artificially strong container wall.

FIG. 5 TEST METHOD

The test methodology includes the ability to measure the load dynamically as the test probe head moves through the sample. In a preferred method, the load is applied at a relatively fast constant speed with force measurements occurring continuously or at small increments of displacement as the test probe head moves through the sample. A currently preferred test probe head displacement rate is approximately 60 inches per minute, which is relatively fast in comparison to the 0.05 inches per minute specified for the different form of testing specified in the ASTM C39-86 standard test procedure. Cellular concrete samples which are deformed in this manner will reach a point of deformation where essentially all the void spaces or cells have been crushed and the amount of compressive force needed for further deformation will rapidly increase or the test sample will experience general structural failure. That point typically occurs at a penetration depth of the order of 80 percent of sample thickness. It is the forces that are necessary to deform the sample from an initial point to the point where this rapid rise in compression force occurs (e.g., to at least 60 percent of sample thickness) that are of interest and which the test methodology and apparatus should seek to capture. Thus, it will be appreciated that an objective of the present invention is to provide test results indicative of deceleration which will be experienced by a vehicle or other object moving through a volume of compressible arresting material. This objective differs from the objective of prior known test approaches which are inadequate for present purposes.

Figure 5:
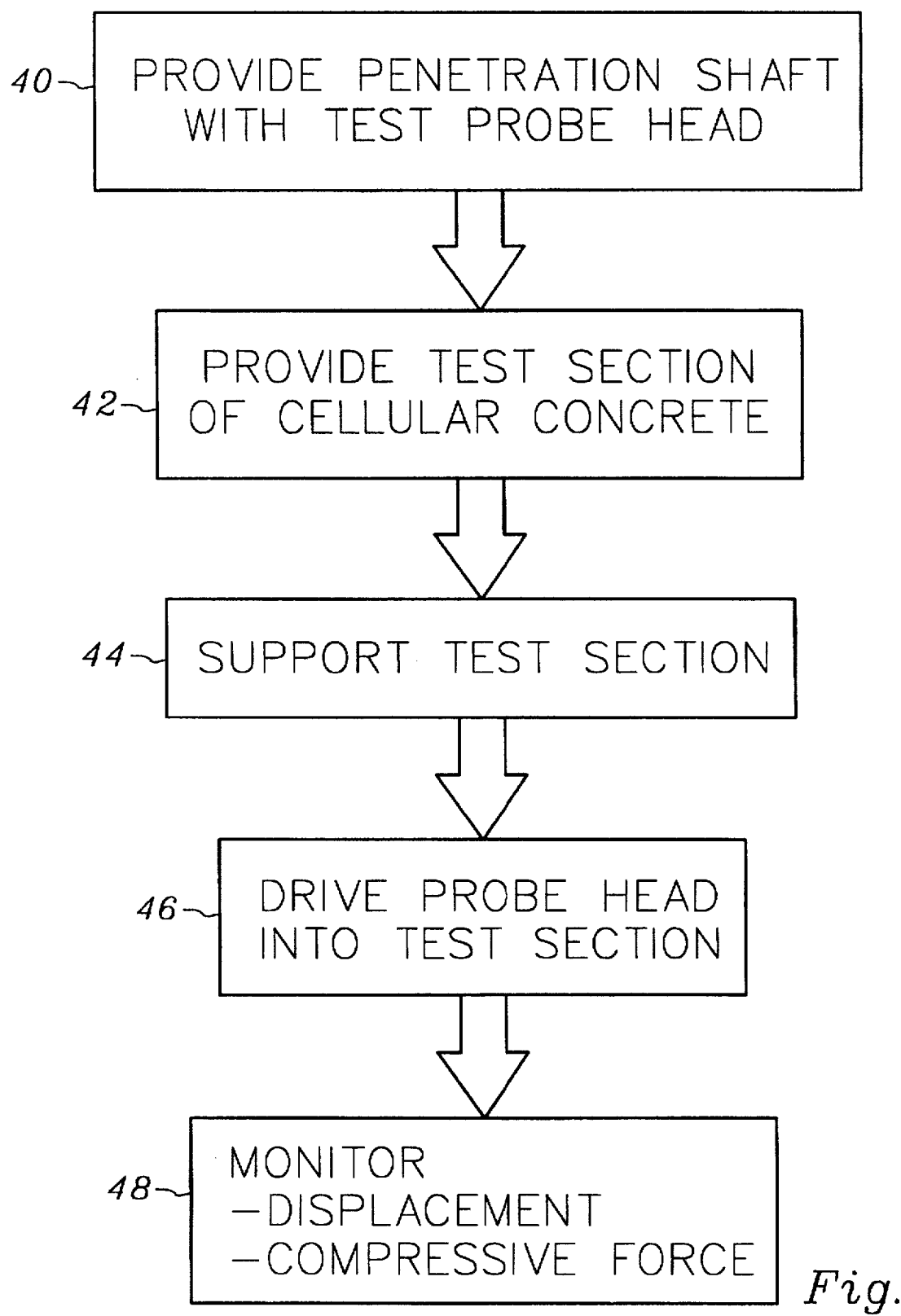
FIG. 5 is a flow chart useful in describing a test method in accordance with the invention.

In accordance with the invention and with reference to FIG. 5, a method for continuous compressive gradient testing of a cellular concrete section suitable for vehicle arresting use, comprises the following steps:

(a) providing, at step 40 in FIG. 5, a penetration shaft bearing a test probe head with a compressive contact surface having a contact surface area;

(b) providing, at step 42, a test section of cellular concrete having a cross-sectional area at least twenty times larger than the contact surface area and having a thickness;

(c) supporting the test section longitudinally, at step 44;

(d) driving the contact surface of the test probe head, at step 46, longitudinally into the test section from the top surface to an internal depth of penetration within the test section;

(e) monitoring, at step 48, displacement of the test probe head; and (f) monitoring, at step 48, compressive force on said contact surface at a plurality of intermediate depths of penetration within said test section.

The method may additionally include the step of making available a presentation of a gradient representing values of compressive force at the plurality of intermediate depths, as will be described with reference to FIGS. 6 and 7. The presentation may take the form of a computer printout as in FIGS. 6 and 7, a comparable display on a computer monitor, or other suitable form.

In application of the test method, step (c) preferably comprises supporting the bottom of the test section, with an absence of lateral restriction of the sides of the test section. Also, step (d) preferably comprises driving the contact surface continuously to an internal depth of penetration equal to at least 60 percent (and typically to about 70 percent) of the thickness of the test section, and in step (e) force on the contact surface of the test probe head is preferably recorded at short intervals (e.g., 10 to 30 times per second) until the contact surface reaches such internal depth of penetration.

The apparatus is arranged to apply the load to the sample continuously rather than intermittently, and without shock. The rate of loading should be adjustable, preferably controllable through software run by the data acquisition means which can, for example, be a general purpose personal computer with appropriate data acquisition software. Preferably, the apparatus provides a prescribed rate of loading for the full stroke during penetration of the test section. Stroke length will vary depending on test section thickness with a longer loaded stroke length for a deeper penetration depth as appropriate for thicker test sections. The load information, distance information, and pressure information is acquired by the data acquisition means during penetration and may be sampled and recorded at a rate of 30 times per second for each individual test. In other applications the sampling rate may be different. While tolerances should be specified as appropriate in particular embodiments, a test specification may provide that the maximum error allowable at any point for load is 3 in 1,000 pounds, for distance is 0.0625 inches in 24 inches, and for pressure 1 in 1,000 psig. Verification of the accuracy of operation and data acquisition should include testing through the full loading range.

The data acquisition software used on the data acquisition computer can be arranged and configured by skilled persons so that it is effective in monitoring all of the information received from each sensing device of the apparatus. Preferably, the software should enable use of a display to permit the operator to continuously display and observe data as the testing occurs. Data to be recorded includes readings representative of load (pounds), displacement (inches) time (seconds), and preferably also hydraulic pressure (psig). Data should typically be sampled at short intervals (e.g., 30 readings per second). This should occur for the full stroke of the test probe head as it penetrates the sample. In certain configurations, hydraulic pressure may not be monitored, or may be utilized as backup or substitute data for loading data. To provide for maximum accuracy, zeroing and adjustment of the test apparatus should be monitored and recorded by the data acquisition software. It may be desirable to record raw incoming data directly and also to automatically make available data in converted form. Thus, for example, load data regarding contact surface force may typically be recorded in pounds and can be converted to psi by factoring in contact surface area. Similarly, a resistance representative voltage output from displacement sensor 24 can be converted to inches of displacement.

Preparation of uniform samples and careful recording with regard to their characteristics is an important part of the testing process. Certain specific observations can be made regarding the testing process. Sampling of cellular concrete may, for example, utilize appropriate provisions of method C-172 of the ASTM with the following exceptions: when sampling from pump equipment, a bucket of approximately 5 gallon capacity should be filled by passing it through the discharge stream of the concrete pump hose being used to place the concrete at the point of placement of the concrete. Care should be exercised to insure that the sample is representative of the pour, avoiding the beginning or ending of the discharge of the equipment. The test specimens should then be prepared, as described below, by pouring lightweight concrete from the bucket. Furthermore, no remixing of samples should be allowed in this test procedure. Typically, test specimens may be 12 inch cubes or have other suitable three-dimensional shapes. Specimens are molded by placing the concrete in a continuous and forceful pouring manner. The molds should be gently shaken as the material is added. The concrete should not be rodded. The specimens should be struck off immediately after filling the molds. They should be covered in a manner to prevent evaporation without marring the surface. The specimens should not be removed from the mold until such time as they are to be tested. Curing of the specimens should desirably occur at about the same curing temperature as used for the arresting bed section of which the specimens are representative. The specimens should remain covered, to restrict evaporation, for at least about 21 days or until tested for compressive strength, in a manner consistent with curing of the corresponding arresting bed sections.

In preparation for testing, the specimen should be removed from the mold and placed beneath the test probe head. The top surface should have a smooth face to accommodate the face of the probe head contact surface. The surface of the specimen in contact with the lower bearing block of the test machine should be flat enough to be stable and prevent skewing of the piston during the test. Prior to the test, the specimen should be weighed and measured along three axes (height, length, width). These dimensions are then used in computing the density as of the time of testing. At the time of the test, the contact surface of the test probe head and the surfaces of the bottom bearing block should be clean and the sample should be carefully aligned so that the test probe head will pass through the approximate center of the specimen. As the contact surface is initially brought to bear on the specimen, the specimen positioning may be gently adjusted by hand. Then continuous load should be applied without shock at a constant rate, typically about 1 inch per second. Data points are preferably recorded to the full depth of penetration. The type of any failure and the appearance of the concrete at completion of testing are preferably recorded and included with the test data.

Compressive gradient strength data is calculated by dividing the load at the data point by the surface area of the piston. Data points during initial displacement up to about 10 percent of test section thickness and data that is captured after the specimen reaches a fully compressed state are typically discarded as less reliable than the remaining test data. The depth of penetration should be calculated by subtracting the piston displacement at initial contact from the last data point of piston displacement.

Figure 6:
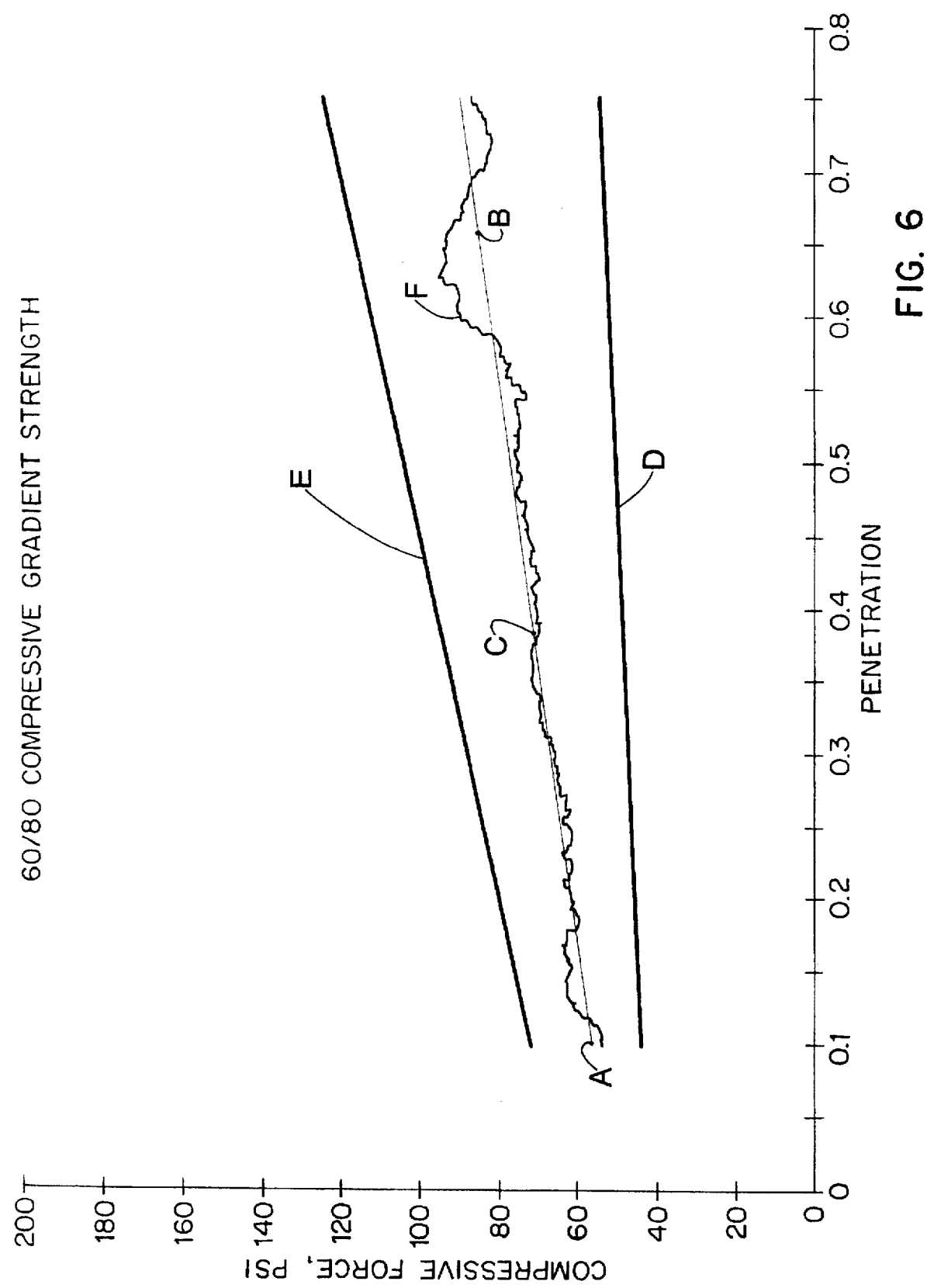

Referring to FIGS. 6 and 7, examples of test data recorded during testing of cellular concrete samples are shown. In this case the test samples were of a size and shape approximating 12 inch cubes. Test data was derived using a test probe head having a flat circular contact surface, with a load cell used to measure loads through 75 percent of the total sample thickness. FIG. 6 illustrates the CGS characteristics of a cellular concrete sample representative of an arresting block, as determined by test. In FIG. 6, the bottom scale represents percentage of test probe penetration expressed in tenths of sample thickness or height. The vertical scale represents test probe compressive force expressed in pounds per square inch (psi). The test data of interest is typically within the range of penetration from 10 to 60 percent of sample thickness. Data outside this range may be less reliable, with total compression effects occurring beyond about 70 percent penetration.

As illustrated in FIG. 6, the failure strength of cellular concrete exhibits a gradient with resistance to compression increasing with depth of penetration. The line through points A and B in FIG. 6 represents a generalized 60/80 CGS, i.e., a CGS characterized by a compression strength changing linearly from approximately 60 psi to approximately 80 psi over a 10 to 66 percent penetration range. The average, over this range is thus approximately 70 psi at mid-point C. Lines D and E represent quality control limits and line F represents actual test data as recorded for a specific test sample of cellular concrete. In this example, a test sample for which test data over a 10 to 66 percent penetration range remains within quality control limit lines D and E, represents an arresting block fabricated within acceptable tolerances. FIG. 7 is a similar illustration of CGS characteristics of a test sample of an 80/100 CGS arresting block.

While there have been described the currently preferred embodiments of the invention, those skilled in the art will recognize that other and further modifications may be made without departing from the invention and it is intended to claim all modifications and variations as fall within the scope of the invention.

What is claimed is:

1. Arresting material test apparatus, to test compressive gradient strength on a continuous basis from the surface to an internal depth of penetration within compressible arresting material, comprising:

a penetration shaft having a length greater than said internal depth of penetration and a cross-sectional size;

a test probe head connected to said penetration shaft and having a compressive contact surface;

said penetration shaft including a constricted shaft portion beginning behind said test probe head and continuing for at least a part of said length, said constricted shaft portion having a cross-sectional area smaller than the area of said contact surface of said test probe;

a drive mechanism coupled to said penetration shaft to displace said shaft to drive said test probe head to said internal depth of penetration within arresting material;

a displacement sensing device coupled to said penetration shaft to sense displacement thereof;

a load sensing device coupled to said penetration shaft to sense the force exerted against said test probe contact surface as it compresses arresting material to said internal depth of penetration; and a data acquisition device responsive to force sensed by said load sensing device and to the depth of penetration of said test probe contact surface to provide data representative of compressive gradient strength of said compressible arresting material to said depth of penetration.

2. Arresting material test apparatus as in claim 1, wherein said cross-sectional area of the constricted shaft portion is smaller than the area of said test probe contact surface by an amount effective to reduce distortive effects of post-compression build-up of particles of cellular concrete during testing of cellular concrete arresting material.

3. Arresting material test apparatus as in claim 1, wherein said test apparatus is arranged to drive said test probe head to an internal depth of penetration of at least 60 percent of the thickness of cellular concrete arresting material while exerting a force of up to at least 100 psi against said test probe head.

4. Arresting material test apparatus as in claim 1, wherein said data acquisition device has a capability to provide data representative of compressive gradient strength, at increments of penetration from the surface of a section of compressible arresting material to an internal depth of penetration within said section.

5. Arresting material test apparatus as in claim 1, wherein said test probe head has a flat contact surface and said constricted shaft portion has a cross-sectional area at least ten percent smaller than the area of said contact surface.

6. Arresting material test apparatus as in claim 1, wherein said test probe head has a flat circular contact surface with an area in a range from 1 to 4 square inches.

7. Arresting material test apparatus as in claim 1, wherein said constricted shaft portion of said penetration shaft continues behind said test probe head for at least the intended depth of penetration and has a cross-sectional area in a range of 10 to 50 percent smaller than said contact surface.

8. Arresting material test apparatus as in claim 1, wherein said drive mechanism includes a hydraulic cylinder mated to said cross-sectional size of said penetration shaft and providing a capability of exerting test probe head pressure in a range to at least 150 psi over a displacement from the surface of a section of compressible arresting material to a penetration depth equal to at least 60 percent of the thickness of said section.

9. Arresting material test apparatus as in claim 1, wherein said load continuously sensing device has a capability to sense force on said test probe head in a range to at least 100 psi as said test probe head is displaced from the surface of a section of compressible arresting material to a penetration depth equal to at least 60 percent of the thickness of said section.

10. An arresting material test probe, suitable to test compressive gradient strength continuously from the surface to an internal depth of penetration within compressible arresting material, comprising:

a penetration shaft having a length not less than said internal depth of penetration and a cross-sectional size; and a test probe head connected to said penetration shaft and having a compressive contact surface;

said penetration shaft including a constricted shaft portion, beginning behind said test probe head and continuing for at least a part of said length, said constricted shaft portion having a smaller cross-sectional area than the area of said contact surface of said test probe;

the smaller cross-sectional area of said constricted shaft portion being effective to reduce distortive effects of post-compression build-up of material behind said contact surface as it travels from the surface to said internal depth of penetration within compressible arresting material under test, and the combination of said compressive contact surface and smaller cross-sectional area of said constricted shaft portion being effective to enable determination of compressive gradient strength over said depth of penetration within a section of compressible arresting material to be tested.

11. An arresting material test probe as in claim 10, wherein said test probe head has a flat circular contact surface.

12. An arresting material test probe as in claim 10, wherein said test probe head has a flat contact surface with an area in a range from 1 to 4 square inches.

13. An arresting material test probe as in claim 12, wherein said contact surface is circular.

14. An arresting material test probe as in claim 10, wherein said constricted shaft portion of said penetration shaft continues behind said test probe head for at least the intended depth of penetration and has a cross-sectional area in a range of 10 to 50 percent smaller than said contact surface.

15. An arresting material test probe as in claim 10, wherein said penetration shaft and test probe head are constructed to withstand compressive forces associated with a test probe head pressure in a range to at least 150 psi.

16. An arresting material test probe as in claim 10, wherein said contact surface of said test probe head has a surface hardness adequate to survive compression testing of cellular concrete to pressures of at least 150 psi, without significant surface distortion.

17. A method for continuous compressive testing of a cellular concrete section suitable for arresting motion of an object, comprising the steps of:

(a) providing a penetration shaft bearing a test probe head with a compressive contact surface having a contact surface area;

(b) providing a test section of cellular concrete having a thickness and having a cross-sectional area larger than said contact surface area;

(c) supporting said test section longitudinally;

(d) driving said contact surface of said test probe head longitudinally into said test section from a surface to an internal depth of penetration within said test section;

(e) monitoring displacement of said test probe head; and (f) monitoring compressive force on said contact surface at a plurality of intermediate depths of penetration within said test section.

18. A method as in claim 17, wherein step (a) comprises providing said penetration shaft with a constricted shaft portion beginning behind said test probe head, said constricted shaft portion having a smaller cross-sectional area than said contact surface area, said smaller cross-sectional area being effective to reduce distortive effects of post-compression build-up of material behind said test probe head during penetration of said cellular concrete section.

19. A method as in claim 18, wherein said penetration shaft is provided with a shaft portion having a cross-sectional area in a range of 10 to 50 percent smaller than contact surface area.

20. A method as in claim 17, wherein step (a) comprises providing said test probe head with a flat circular contact surface.

21. A method as in claim 17, wherein step (a) comprises providing said test probe head with a flat contact surface having a contact surface area in a range from 1 to 4 square inches.

22. A method as in claim 21, wherein said test probe head is provided with a circular contact surface.

23. A method as in claim 17, wherein step (b) comprises providing said test section having a cross-sectional area at least twenty times larger than said contact surface area.

24. A method as in claim 17, wherein step (c) comprises supporting the bottom of said test section, with an absence of lateral restriction of the sides of said test section.

25. A method as in claim 17, wherein step (d) comprises driving said contact surface continuously to an internal depth of penetration equal to at least 60 percent of the thickness of said test section.

26. A method as in claim 17, wherein step (f) comprises recording pressure on the contact surface of said test probe head on a continuous basis until said contact surface reaches an internal depth of penetration of at least 60 percent of the thickness of said test section.

27. A method for determining compressive gradient strength over a depth of penetration of a test section, comprising the steps of:
    (a) driving a contact surface into said test section to an internal depth of penetration within said test section equal to at least 60 percent of the thickness of said test section;
    (b) during step (a), recording a measure of compressive force on said contact surface for a plurality of intermediate depths of penetration within said test section; and
    (c) making available a presentation of a gradient representing values of compressive force at said plurality of intermediate depths of penetration.

28. A method as in claim 27, wherein step (a) comprises driving a contact surface into a test section of cellular concrete.

29. A method as in claim 27, wherein step (a) includes using a contact surface having an area not greater than 5 percent of the cross-sectional area of said test section.

30. A method for determining compressive gradient strength over a depth of penetration of a test section of compressible material, comprising the steps of:
    (a) driving a flat contact surface into said test section to compress said compressible material from a surface to an internal depth of penetration within said test section;
    (b) during compression in step (a), recording a measure of compressive force on said contact surface for a plurality of intermediate depths of penetration within said test section; and
    (c) making available a presentation of compressive gradient strength representing values of compressive force at said plurality of intermediate depths of penetration during compression of said compressible material.

31. A method as in claim 30, wherein step (a) comprises driving a contact surface into a test section of cellular concrete.

32. A method as in claim 30, wherein step (b) comprises recording compressive force in pounds at least ten times per second while step (a) is implemented.

33. A method as in claim 30, wherein step (c) comprises making available a gradient in the form of a line joining points each representing a value of compressive force at an intermediate depth of penetration within said test section.

34. A method as in claim 33, wherein said gradient is made available as a computer printout.

* * * * *